United States Patent
Lee et al.

(10) Patent No.: US 12,257,563 B2
(45) Date of Patent: Mar. 25, 2025

(54) ALDOL CONDENSATION REACTION APPARATUS

(71) Applicant: HANWHA SOLUTIONS CORPORATION, Seoul (KR)

(72) Inventors: Shinbeom Lee, Daejeon (KR); Hyojin Jeon, Daejeon (KR); Gyeongseon Jeong, Daejeon (KR); Keedo Han, Daejeon (KR); Junhee Han, Daejeon (KR)

(73) Assignee: HANWHA SOLUTIONS CORPORATION, Seoul (KR)

( * ) Notice: Subject to any disclaimer, the term of this patent is extended or adjusted under 35 U.S.C. 154(b) by 232 days.

(21) Appl. No.: 17/767,429

(22) PCT Filed: Aug. 5, 2020

(86) PCT No.: PCT/KR2020/010299
§ 371 (c)(1),
(2) Date: Apr. 7, 2022

(87) PCT Pub. No.: WO2021/071073
PCT Pub. Date: Apr. 15, 2021

(65) Prior Publication Data
US 2024/0091737 A1  Mar. 21, 2024

(30) Foreign Application Priority Data

Oct. 8, 2019  (KR) .................. 10-2019-0124798

(51) Int. Cl.
*B01J 19/24*  (2006.01)
*B01D 17/02*  (2006.01)
(Continued)

(52) U.S. Cl.
CPC ............ *B01J 19/248* (2013.01); *B01D 17/02* (2013.01); *B01J 19/0013* (2013.01);
(Continued)

(58) Field of Classification Search
CPC ........ B01D 17/00; B01D 17/02; C07C 45/00; C07C 45/45; C07C 45/61; C07C 45/67;
(Continued)

(56) References Cited

U.S. PATENT DOCUMENTS

| 2014/0144821 A1* | 5/2014 | Sitkiewitz ............... C02F 1/325 |
| | | 210/96.1 |
| 2014/0155656 A1 | 6/2014 | Krokoszinski |
| 2018/0179140 A1* | 6/2018 | Marras ..................... B01J 35/19 |

FOREIGN PATENT DOCUMENTS

| CN | 102442893 A | 5/2012 |
| CN | 104080760 A | 10/2014 |

(Continued)

OTHER PUBLICATIONS

Machine translation of KR 101378265 B1 (Year: 2014).*
(Continued)

*Primary Examiner* — Natasha E Young
(74) *Attorney, Agent, or Firm* — Harvest IP Law, LLP

(57) ABSTRACT

Provided is an apparatus for an aldol condensation reaction having high productivity at low cost. Specifically, the apparatus for an aldol condensation reaction according to the present invention has an effect of having high productivity by preventing a drop in a conversion rate due to an increase in a residence time when increasing a facility scale, allows conditions of raising a concentration of a catalyst and a temperature, and has an effect of minimizing a content of the catalyst used at the same yield as compared with a conventional apparatus. In addition, costs required for increasing a facility scale may be minimized without adding a device such as a pump separately, and an amount of harmful wastewater produced may be minimized.

7 Claims, 1 Drawing Sheet

(51) Int. Cl.
  *B01J 19/00* (2006.01)
  *B01J 23/04* (2006.01)
  *B01J 35/27* (2024.01)
  *C07C 45/45* (2006.01)
  *C07C 45/80* (2006.01)

(52) U.S. Cl.
  CPC .......... *B01J 19/0066* (2013.01); *B01J 23/04* (2013.01); *B01J 35/27* (2024.01); *C07C 45/45* (2013.01); *C07C 45/80* (2013.01); *B01J 2219/00033* (2013.01); *B01J 2219/00063* (2013.01); *B01J 2219/00103* (2013.01); *B01J 2219/00166* (2013.01)

(58) Field of Classification Search
  CPC .......... C07C 45/68; C07C 45/72; C07C 45/74; C07C 45/78; C07C 45/80; C07C 47/00; C07C 47/02
  See application file for complete search history.

(56) References Cited

FOREIGN PATENT DOCUMENTS

| KR | 1019980028461 A | 7/1998 |
| KR | 1020060073044 A | 6/2006 |
| KR | 20120032701 A | 4/2012 |
| KR | 20120035368 A | 4/2012 |
| KR | 101378265 B1 * | 3/2014 |
| WO | 2013095766 A1 | 6/2013 |

OTHER PUBLICATIONS

The Notice of allowance issued on Jun. 5, 2024.
CN OA issued on Feb. 15, 2023.
An European search report issued on Oct. 4, 2023 for corresponding EP Patent Application.

* cited by examiner

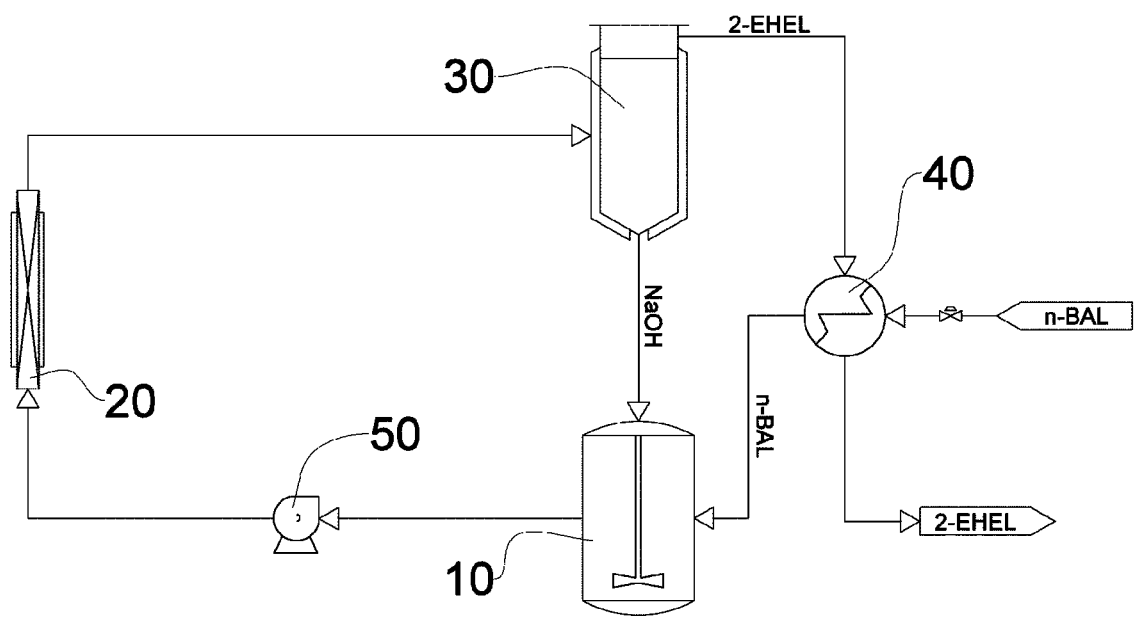

ALDOL CONDENSATION REACTION APPARATUS

CROSS-REFERENCE TO RELATED APPLICATIONS

This application is a National Stage of International Application No. PCT/KR2020/010299, now WO 2021/071073, filed Aug. 5, 2020, claiming priority based on Korean Patent Application No. 10-2019-0124798, filed Oct. 8, 2019, the disclosure of which is incorporated herein by reference in its entirety.

TECHNICAL FIELD

The present invention relates to an apparatus for an aldol condensation reaction.

BACKGROUND ART

In general, an aldol condensation reaction refers to a process in which various olefins and synthetic gas ($CO/H_2$) are reacted by a hydroformylation reaction known as an oxo reaction in the presence of a metal catalyst and a ligand to produce linear and branched aldehydes having one more carbon atoms on the olefin, from which alpha and beta unsaturated aldehydes are produced by an aldol condensation reaction.

The unsaturated aldehyde synthesized after the condensation reaction of an aldol and the like may be converted into various acids and alcohols containing a long alkyl group by an oxidation or reduction reaction, and these alcohols and acids are used as a raw material of solvents, additives, and various plasticizers, and the like.

In order to improve a conventional aldol condensation reaction, Korean Patent Laid-Open Publication No. 10-2004-0111873 discloses that in the technology related to a preparation method of neopentyl glycol, the aldol condensation reaction is performed in continuous stirred tank reactors arranged in series as two or more reactors. In addition, Korean Patent Laid-Open Publication No. 10-1996-0047519 discloses that in the technology related to a preparation method of neopentyl glycol, an unreacted aldehyde recovery column is provided after an aldol condensation reactor, thereby circulating the unreacted material to improve reaction efficiency.

Also, when a plug flow reactor (PFR) is used, a length of the reactor should be increased to usually 70 m or more and even 100 m or more for a required level of a conversion rate and a yield, and thus, it is difficult to secure a space, and equipment for controlling reactor conditions is too much and becomes complicated.

Besides, there has been a limitation in controlling heat of reaction in synthesizing an unsaturated aldehyde from an aldehyde-based compound by the aldol condensation reaction. Until now, a means for controlling a temperature to a desired temperature using a heat exchanger while constantly circulating a reactant has been used, which has poor thermal efficiency due to a large consumption of additional heat energy, and the facility scale thereof becomes large and complicated.

DISCLOSURE

Technical Problem

An object of the present invention is to provide an apparatus for an aldol condensation reaction having high productivity at low cost.

A specific object of the present invention is to provide an apparatus for an aldol condensation reaction having high productivity by preventing a drop in a conversion rate due to an increase in a residence time when increasing a facility scale.

Another specific object of the present invention is to provide an apparatus for an aldol condensation reaction which allows conditions of raising a concentration of a catalyst and a temperature and may minimize a content of a catalyst used at the same yield as compared with the conventional apparatus.

Another specific object of the present invention is to provide an apparatus for an aldol condensation reaction which may minimize costs required for increasing a facility scale even without adding a device such as a pump separately.

Still another specific object of the present invention is to provide an apparatus for an aldol condensation reaction which may minimize an amount of harmful wastewater produced.

Technical Solution

In one general aspect, an apparatus for an aldol condensation reaction which produces 2-ethylhexenal from n-butyraldehyde by an aldol condensation reaction includes: a continuous stirred tank reactor 10 into which n-butyraldehyde and a catalyst flow, a plug flow reactor 20 into which n-butyraldehyde, the catalyst, and a product flow from the continuous stirred tank reactor 10, an oil-water separator 30 into which the product and the catalyst flow from the plug flow reactor 20 and which separates the catalyst with an aqueous layer and separates the product with an organic layer, and a heat exchanger 40 for transferring heat of the separated product to n-butyraldehyde flowing into the continuous stirred tank reactor 10, wherein the catalyst separated as the aqueous layer in the oil-water separator 30 directly flows into the continuous stirred tank reactor 10 and is circulated.

In an exemplary embodiment of the present invention, in the heat exchanger 40, n-butyraldehyde may be heated from room temperature to 70 to 170° C. by the product discharged from the plug flow reactor 20.

The apparatus for an aldol condensation reaction according to an exemplary embodiment of the present invention may further include a storage unit of 2-ethylhexenal into which the product losing heat from n-butyraldehyde by the heat exchanger 40 flows.

In an exemplary embodiment of the present invention, a conversion rate in the continuous stirred tank reactor 10 may be 30 to 60%.

In an exemplary embodiment of the present invention, a conversion rate in the plug flow reactor 20 may be 95% or more.

The apparatus for an aldol condensation reaction according to an exemplary embodiment of the present invention may further include a temperature controller for controlling a reaction temperature of the continuous stirred tank reactor 10 or the plug flow reactor 20 to 80 to 200° C.

The apparatus for an aldol condensation reaction according to an exemplary embodiment of the present invention may further include a residence time controller for controlling a residence time of the continuous stirred tank reactor 10 or the plug flow reactor 20 to 0.1 to 30 minutes.

In an exemplary embodiment of the present invention, the catalyst may include any one or more selected from an aqueous NaOH solution and an aqueous KOH solution.

Advantageous Effects

The apparatus for an aldol condensation reaction according to the present invention has an effect of having high productivity at low cost.

Specifically, the apparatus for an aldol condensation reaction according to the present invention has an effect of having high productivity by preventing a drop in a conversion rate due to an increase in a residence time when increasing a facility scale.

In addition, the apparatus for an aldol condensation reaction according to the present invention allows conditions of raising a concentration of a catalyst and a temperature and may minimize a content of a catalyst used at the same yield as compared with the conventional apparatus.

In addition, the apparatus for an aldol condensation reaction according to the present invention has an effect of minimizing costs required for increasing a facility scale even without adding a device such as a pump separately.

In addition, the apparatus for an aldol condensation reaction according to the present invention has an effect of minimizing an amount of harmful wastewater produced.

DESCRIPTION OF DRAWINGS

FIG. 1 is a process diagram which schematically illustrates the apparatus for an aldol condensation reaction according to the present invention.

BEST MODE

Hereinafter, the apparatus for an aldol condensation reaction according to the present invention will be described in detail with reference to the accompanying drawing.

The drawings illustrated in the present specification are provided by way of example so that the idea of the present invention may be sufficiently conveyed to a person skilled in the art. Therefore, the present invention is not limited to the provided drawings, but may be embodied in many different forms, and the drawings may be exaggerated in order to clear the spirit of the present invention.

Technical terms and scientific terms used in the present specification have the general meaning understood by those skilled in the art to which the present invention pertains unless otherwise defined, and a description for the known function and configuration obscuring the gist of the present invention will be omitted in the following description and the accompanying drawings.

The singular form of the term used herein may be intended to also include a plural form, unless otherwise indicated.

The unit of % used herein without particular mention refers to % by weight, unless otherwise defined.

Until now, when 2-ethylhexenal was intended to be produced from n-butyraldehyde using an aldol condensation reaction, in particular, when a manufacturing facility and equipment were increased for mass production, there were limitations in that it was very difficult to induce the reaction to proceed in the entire area inside a reactor as compared with the case before increasing production, a conversion rate was not high, and it was necessary to secure a very large space for obtaining a required conversion rate or higher.

Thus, the present invention provides an apparatus for an aldol condensation reaction which does not need to secure an additional large space as compared with a conventional apparatus, of course, even in the case of greatly increasing production so that required output is satisfied, minimizes an average diameter of the organic layer particles dispersed in the aqueous layer during the reaction, and allows the reaction state to be maintained in the entire area inside the reactor, and has not only a high reaction area and high efficiency but also may implement an effect of allowing process control of low uncertainty and a high degree of precision in spite of establishment of an increased mass production system. Besides, the present invention has a significantly decreased energy consumption at the same output and excellent economic feasibility by high thermal efficiency as compared with the conventional apparatus.

The apparatus for an aldol condensation reaction according to the present invention, which produces 2-ethylhexenal from n-butyraldehyde by an aldol condensation reaction, includes: a continuous stirred tank reactor (CSTR) 10 into which n-butyraldehyde and a catalyst flow; a plug flow reactor (PFR) 20 into which n-butyraldehyde, the catalyst, and a product flow from the continuous stirred tank reactor 10; an oil-water separator 30 into which the product and the catalyst flow from the plug flow reactor 20 and which separates the catalyst with an aqueous layer and separates the product with an organic layer; and a heat exchanger 40 for transferring heat of the product to n-butyraldehyde flowing into the continuous stirred tank reactor 10, wherein the catalyst separated as the aqueous layer in the oil-water separator 30 directly flows into the continuous stirred tank reactor 10 and is circulated.

In the present invention, the catalyst separated as an aqueous layer in the oil-water separator 30 directly flows into the continuous stirred tank reactor 10 and is circulated, and high heat of 2-ethylhexenal as the product is not discarded as waste heat but transferred to n-butyraldehyde as the reactant, thereby having an effect of synthesizing 2-ethylhexenal at a high conversion rate and a high yield even in a larger scale mass production system as compared with a conventional system. Therefore, in the present invention, the catalyst allows the continuous stirred tank reactor 10, the plug flow reactor 20, and the oil-water separator 30 to be constantly circulated.

The fact that "the catalyst separated in the oil-water separator 30 as an aqueous layer directly flows into the continuous stirred tank reactor 10 and is circulated" means that the catalyst circulated through the oil-water separator 30 does not flow into the reactor via a supply line in which the reactant is transferred, but flows into the continuous stirred tank reactor 10. That is, in the present invention, the catalyst to be circulated does not flow into the supply line to be transferred to flow into the continuous stirred tank reactor 10 in a mixed state of the catalyst and the reactant. As before, when the catalyst to be circulated through the oil-water separator 30 is mixed with the reactant and then flows into the continuous stirred tank reactor 10 via a mixing supply line, particularly in the case of a mass production system having a large volume of the reaction area by a production increase, it is practically difficult to precisely control process conditions, and thus, in the entire area inside the reactor, it is difficult to maintain a reaction state in which an average diameter of organic layer particles dispersed in an aqueous layer during the reaction is minimized. This may cause decreases in the conversion rate and the yield, that is, a decrease in the output. It is preferred that the aldol condensation reaction to synthesize a product from a reactant by a catalyst occurs inside a reactor having an environment satisfying process conditions, and when the reaction occurs in the mixing supply line or the like which does not satisfy the conditions, it is difficult to control the process, uncertainty is increased, and it is difficult to have the conversion rate at or above a required level, due to an action of various variables.

N-butyraldehyde discharged through the heat exchanger 40 flows into the continuous stirred tank reactor 10 in the state of having increased heat as compared with n-butyraldehyde before flowing into the heat exchanger 40. Further, 2-ethylhexenal discharged through the heat exchanger 40 is discharged in the state of having decreased heat as compared with 2-ethylhexenal before flowing into the heat exchanger 40. Here, the discharged 2-ethylhexenal may be stored in a storage unit of 2-ethylhexenal. That is, the apparatus for an aldol condensation reaction according to an exemplary embodiment of the present invention may further include the storage unit of 2-ethylhexenal into which the product losing heat from n-butyraldehyde by the heat exchanger 40 flows.

A temperature of n-butyraldehyde receiving heat from the product by the heat exchanger 40 may be adjusted depending on reaction conditions, but preferably, in the heat exchanger 40, n-butyraldehyde may be heated from room temperature to 70 to 170° C. by the product discharged from the plug flow reactor 20.

For a reaction temperature of the continuous stirred tank reactor 10 or the plug flow reactor 20, known literature may be referred, and as an example, the temperature may be 80 to 200° C., specifically 100 to 160° C. That is, the apparatus for an aldol condensation reaction according to an exemplary embodiment of the present invention may further include a temperature controller for controlling the reaction temperature of each of the reactors 10 and 20 to 70 to 170° C.

In particular, as described above, since the product exchanges heat with the reactant, the temperature automatically approaches a required reaction temperature, and a temperature range to be controlled in the temperature controller is reduced as compared with a conventional range to allow control of a more precise temperature.

As described above, the apparatus for an aldol condensation reaction according to the present invention may produce 2-ethylhexenal from n-butyraldehyde by a continuous process, induce the product having high heat by heat of reaction generated during the aldol condensation reaction to more easily equilibrate toward room temperature, and simultaneously, efficiently supply heat required for the reaction to the reactant.

Since the continuous stirred tank reactor 10 is already known in the chemical engineering field, it may be designed referring to known literature, but it is preferred that a reaction area volume is 0.6 to 1 m3, in terms of being more helpful for improving the conversion rate.

The plug flow reactor 20 may be easily designed referring to the known literature, and as an example, the inside of the reactor may be provided with spiral continuous members having constant or inconstant pitches along a length direction of a tube, but the present invention is not limited thereto, of course.

The oil-water separator 30 is a device for phase-separating an organic layer in the upper portion and an aqueous layer in the lower portion from the mixture including the catalyst and the product, and for the details thereof, the known literature may be referred. 2-ethylhexenal as the product is present in the organic layer and the catalyst is present in the aqueous layer, and 2-ethylhexenal is discharged through an upper pipe of the oil-water separator 30 and the catalyst is discharged through a lower pipe of the oil-water separator 30.

The conversion rate in the continuous stirred tank reactor 10 may be preferably in a range of 30 to 60% and specifically in a range of 35 to 55%, and the conversion rate in the plug flow reactor 20 may be in a range of 95% or more, specifically 97% or more, and more specifically 97% to 99.9%. When the conversion rates in the range described above in the continuous stirred tank reactor 10 and the plug flow reactor 20 are satisfied, respectively, a final result may be a high conversion rate and a high yield of 95% or more, preferably 97% or more.

That is, the apparatus for an aldol condensation reaction according to a preferred exemplary embodiment may further include a residence time controller so that the conversion rate in the continuous stirred tank reactor 10 may be 30 to 60% and specifically 35 to 55% and the conversion rate in the plug flow reactor 20 may be 95% or more, specifically 97% or more, and more specifically 97% to 99.9%.

The residence time controller may control the residence time in the continuous stirred tank reactor 10 or the plug flow reactor 20, the residence time may be appropriately controlled so that the conversion rate described above is satisfied, and for example, the residence time may be controlled to 0.1 to 30 minutes, specifically 0.5 to 5 minutes. However, this is described as a preferred example, and the present invention is not interpreted as being necessarily limited thereto.

For a reaction pressure of the continuous stirred tank reactor 10 or the plug flow reactor 20, known literature may be referred, and as an example, the pressure may be in a range of 1 to 50 bar and specifically 2 to 10 bar. That is, the apparatus for an aldol condensation reaction according to an exemplary embodiment of the present invention may further include a pressure controller for controlling the pressure of each of the reactors 10 and 20 to the above range.

In an exemplary embodiment of the present invention, both a base catalyst and an acid catalyst may be used as the catalyst, and for example, it is more preferred to use a base catalyst, and as the base catalyst, a catalyst including any one or more selected from an aqueous NaOH solution, an aqueous KOH solution, and the like may be exemplified. However, this is described as a specific and preferred example, and the present invention is not interpreted as being necessarily limited thereto.

In the present invention, the reactant is reacted in a liquid phase by the catalyst to synthesize a product, the reaction occurs in a liquid phase, and a solution including the reactant, the catalyst, and/or the product may be transferred by a pump 50. A position of the pump 50 is not largely limited, and as an example, may be provided between the continuous stirred tank reactor 10 and the plug flow reactor 20, as shown in FIG. 1. However, this is described as a specific example, and the present invention is not interpreted as being necessarily limited thereto.

In the continuous stirred tank reactor 10 or the plug flow reactor 20, for a flow rate of the solution including the reactant, the catalyst, and/or the product, known literature may be referred, and as an example, the flow rate may be in a volume flow rate range of 50 to 200 m3/hg. That is, the aldol condensation reaction apparatus according to an exemplary embodiment of the present invention may further include a flow rate controller for controlling the flow rate of the solution in each of the reactors 10 and 20 to the above range.

Hereinafter, the present invention will be described in detail by the Examples, however, the Examples are for describing the present invention in more detail, and the scope of the present invention is not limited to the following Examples.

Example 1

A reaction apparatus as shown in FIG. 1 was designed and 2-ethylhexenal was produced from n-butyraldehyde by the aldol condensation reaction under the conditions of the following Table 1, and the conversion rate was measured.

The catalyst to be circulated by the oil-water separator 30 was not mixed with the reactant, and directly flowed into the continuous stirred tank reactor 10.

Comparative Example 1

The process was performed in the same manner as in Example 1, except that the catalyst circulated by the oil-water separator 30 flowed into the continuous stirred tank reactor 10 in the state of being mixed with the reactant via a supply line transferring the reactant.

TABLE 1

|  | CSTR | | PFR | |
| --- | --- | --- | --- | --- |
|  | IN | OUT | IN | OUT |
| Temperature (° C.) | 120.3 | 134 | 134 | 148 |
| Pressure (bar) | 6.5 | 6.5 | 6.5 | 6.51 |
| Mass flowrate (kg/hr) | 78723.9 | 78723.9 | 78723.9 | 78723.9 |
| Volume flowrate (m³/hr) | 92.75 | 94.13 | 94.13 | 94.78 |
| Reactor volume (m³) | 0.6 | | 1.37 | |
| Diameter (mm) | 750 | | — | |
| Height (mm) | 1,140 | | — | |
| Residence time (sec) | 23 | | 52 | |
| Conversion rate (%) | 50 | | 96.9 | |
| Total conversion rate (%) | | 97.8 | | |

As a result, in Example 1, a high conversion rate of 97.8% was confirmed, while in Comparative Example 1, a relatively low conversion rate of 95.3% was confirmed. Therefore, it was found to be preferred that the catalyst to be circulated through the oil-water separator 30 does not flow into the continuous stirred tank reactor 10 in the state of being mixed with the reactant via the supply line transferring the reactant, that is, the catalyst to be circulated through the oil-water separator 30 is not mixed with the reactant and directly flows into the continuous stirred tank reactor 10.

The invention claimed is:

1. An apparatus for an aldol condensation reaction which produces 2-ethylhexenal from n-butyraldehyde by an aldol condensation reaction, the apparatus comprising:
   a continuous stirred tank reactor 10 into which n-butyraldehyde and a catalyst flow,
   a plug flow reactor 20 into which n-butyraldehyde, the catalyst, and a product flow from the continuous stirred tank reactor 10,
   an oil-water separator 30 into which the product and the catalyst flow from the plug flow reactor 20 and which separates the catalyst with an aqueous layer and separates the product with an organic layer, and
   a heat exchanger 40 for transferring heat of the separated product to n-butyraldehyde flowing into the continuous stirred tank reactor 10,
   wherein the catalyst separated as the aqueous layer in the oil-water separator 30 directly flows into the continuous stirred tank reactor 10 and is circulated.

2. The apparatus for an aldol condensation reaction of claim 1, wherein
   in the heat exchanger 40, n-butyraldehyde is heated from room temperature to 70 to 170° C. by the product discharged from the plug flow reactor 20, and
   a temperature of n-butyraldehyde receiving heat from the product by the apparatus for an aldol condensation reaction is 50 to 200° C.

3. The apparatus for an aldol condensation reaction of claim 1, wherein a conversion rate in the continuous stirred tank reactor 10 is 30 to 60%.

4. The apparatus for an aldol condensation reaction of claim 3, wherein a conversion rate in the plug flow reactor 20 is 95% or more.

5. The apparatus for an aldol condensation reaction of claim 1, further comprising: a temperature controller for controlling a reaction temperature of the continuous stirred tank reactor 10 or the plug flow reactor 20 to 80 to 200° C.

6. The apparatus for an aldol condensation reaction of claim 1, further comprising: a residence time controller for controlling a residence time of the continuous stirred tank reactor 10 or the plug flow reactor 20 to 0.1 to 30 minutes.

7. The apparatus for an aldol condensation reaction of claim 1, wherein the catalyst is an aqueous basic solution including any one or more selected from an aqueous NaOH solution and an aqueous KOH solution.

* * * * *